(12) United States Patent
Jonishi et al.

(10) Patent No.: US 9,316,584 B2
(45) Date of Patent: Apr. 19, 2016

(54) SCINTILLATOR PANEL AND RADIATION DETECTOR

(71) Applicant: HAMAMATSU PHOTONICS K.K., Hamamatsu-shi, Shizuoka (JP)

(72) Inventors: Hidenori Jonishi, Hamamatsu (JP); Munenori Shikida, Hamamatsu (JP); Yutaka Kusuyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/414,956

(22) PCT Filed: Apr. 18, 2013

(86) PCT No.: PCT/JP2013/061509
§ 371 (c)(1),
(2) Date: Jan. 15, 2015

(87) PCT Pub. No.: WO2014/013771
PCT Pub. Date: Jan. 23, 2014

(65) Prior Publication Data
US 2015/0198529 A1    Jul. 16, 2015

(30) Foreign Application Priority Data
Jul. 20, 2012    (JP) .................................. 2012-161762

(51) Int. Cl.
| G01T 1/10 | (2006.01) |
| G01N 21/64 | (2006.01) |
| G01T 1/202 | (2006.01) |
| G01T 1/20 | (2006.01) |
| C03C 17/34 | (2006.01) |
| G21K 4/00 | (2006.01) |

(52) U.S. Cl.
CPC ............ *G01N 21/64* (2013.01); *C03C 17/3405* (2013.01); *G01T 1/202* (2013.01); *G01T 1/2018* (2013.01); *C03C 2217/70* (2013.01);
(Continued)

(58) Field of Classification Search
CPC .......................... G01T 1/2018; G01T 1/2002
See application file for complete search history.

(56) References Cited

U.S. PATENT DOCUMENTS 3,855,035 A * 12/1974 Bates et al. .................... 156/276
2003/0001101 A1 * 1/2003 Homme et al. ........... 250/370.11
(Continued)

FOREIGN PATENT DOCUMENTS

| JP | 2003-262671 A | 9/2003 |
| JP | 2005-114680 A | 4/2005 |

(Continued)

OTHER PUBLICATIONS

English-language translation of International Preliminary Report on Patentability (IPRP) dated Jan. 29, 2015 that issued in WO Patent Application No. PCT/JP2013/061509.

*Primary Examiner* — Kiho Kim
(74) *Attorney, Agent, or Firm* — Drinker Biddle & Reath LLP

(57) ABSTRACT

In a scintillator panel, a glass substrate with the thickness of not more than 150 μm serves as a support body, thereby achieving excellent radiotransparency and flexibility. Furthermore, in this scintillator panel, an organic resin layer is formed so as to cover the entire surface of the glass substrate. This reinforces the glass substrate, whereby the edge part thereof can be prevented from chipping or cracking. Furthermore, stray light can be prevented from entering a side face of the glass substrate and, since the organic resin layer is formed on the entire surface, it becomes feasible to suppress warping of the glass substrate due to internal stress after formation of a scintillator layer.

4 Claims, 3 Drawing Sheets

(52) U.S. Cl.
CPC ............ *G21K 4/00* (2013.01); *G21K 2004/10* (2013.01); *Y10T 428/239* (2015.01)

(56) References Cited

U.S. PATENT DOCUMENTS

2006/0033032 A1* 2/2006 Inoue et al. .............. 250/370.11
2009/0065705 A1* 3/2009 Fuchs et al. .............. 250/370.11
2010/0006762 A1* 1/2010 Yoshida et al. ........... 250/361 R
2012/0211669 A1* 8/2012 Itaya .................... G01V 5/0025
250/458.1

FOREIGN PATENT DOCUMENTS

| | | |
|---|---|---|
| JP | 2006-058124 A | 3/2006 |
| JP | 2007-279051 A | 10/2007 |
| WO | WO-2008/117821 A1 | 10/2008 |
| WO | WO-2009028275 A1 | 3/2009 |

* cited by examiner (a)

(b)

(a)

(b)

SCINTILLATOR PANEL AND RADIATION DETECTOR

TECHNICAL FIELD

The present invention relates to a scintillator panel and a radiation detector.

BACKGROUND ART

As a conventional scintillator panel there is, for example, the one described in Patent Literature 1. In this conventional configuration, a 0.05-mm glass substrate is used as a support body for a scintillator layer. Furthermore, a buffer to relieve force from the outside of a housing and a high-stiffness member with stiffness higher than that of the scintillator layer are disposed between the housing and the scintillator layer.

In the scintillator panel described in Patent Literature 2, a graphite substrate coated with a polyimide-based resin film or with a poly-para-xylylene film is used as a support body. Furthermore, in the scintillator panel described in Patent Literature 3, the entire surface of the substrate comprised of amorphous carbon or the like is covered by an intermediate film such as a poly-para-xylylene film.

CITATION LIST

Patent Literatures

Patent Literature 1: Japanese Patent Application Laid-open Publication No. 2006-58124
Patent Literature 2: International Publication WO 2009/028275 Patent Literature 3: Japanese Patent Application Laid-open Publication No, 2007-279051

SUMMARY OF INVENTION

Technical Problems

The scintillator panel applied, for example, to a solid-state detector such as a thin-film transistor (TFT) panel is required to have flexibility enough to satisfy shape-following capability to the solid-state detector. In addition, if there is a difference between the coefficient of thermal expansion of the TFT panel and the coefficient of thermal expansion of the substrate of the scintillator panel, fine flaws on the substrate of the scintillator panel or flaws made between the scintillator panel and the TFT panel by abnormally grown portions produced in formation of the scintillator layer by evaporation can transfer to the light receiving surface because of heat during operation, raising a problem that effort of calibration becomes troublesome.

For solving the problem of flexibility and the problem of coefficient of thermal expansion as described above, it is conceivable to use extremely thin glass, e.g., in the thickness of not more than 150 µm as the substrate of the scintillator panel. However, when the extremely thin glass is used, there arises a problem that the end (edge part) of glass is brittle under an impact to chip or crack.

The present invention has been accomplished in order to solve the above problems and it is an object of the present invention to provide a scintillator panel capable of ensuring satisfactory flexibility while preventing the glass substrate from chipping or cracking, and a radiation detector using it.

Solution to Problems

In order to solve the above problems, a scintillator panel according to the present invention comprises: a glass substrate with a thickness of not more than 150 µm having radiotransparency; a first organic resin layer formed so as to cover the entire surface of the glass substrate; a scintillator layer formed on a one face side of the glass substrate on which the first organic resin layer is formed; and a moisture-resistant protection layer formed so as to cover the whole of the scintillator layer along with the glass substrate on which the first organic resin layer is formed.

In this scintillator panel, the glass substrate with the thickness of not more than 150 µm serves as a support body, thereby to achieve excellent radiotransparency and flexibility and also relieve the problem of thermal expansion coefficient. In addition, in this scintillator panel the first organic resin layer is formed so as to cover the entire surface of the glass substrate. This reinforces the glass substrate, whereby the edge part thereof can be prevented from chipping or cracking. Furthermore, stray light can be prevented from entering the side face of the glass substrate, and warping of the glass substrate can be suppressed because the first organic resin layer is formed on the entire surface thereof.

In the foregoing scintillator panel, the first organic resin layer may be selected from poly-para-xylylen and polyurea.

Furthermore, preferably, a resin film layer is stuck between an other face side of the glass substrate on which the first organic resin layer is formed, and the protection layer. In this case, the glass substrate can be further reinforced by the resin film layer. The resin film layer is present on the other face side of the glass substrate, whereby internal stress of the scintillator layer can be cancelled, so as to more effectively suppress warping of the glass substrate.

Furthermore, preferably, a resin film layer is stuck between the one face side of the glass substrate on which the first organic resin layer is formed, and the scintillator layer. In this case, the glass substrate can be further reinforced by the resin film layer. In addition, transparency can be ensured for light incident to the other face side of the glass substrate, so as to maintain resolution.

In the foregoing scintillator panel, the resin film layer may be selected from PET, PEN, COP, and PI.

Furthermore, preferably, a second organic resin layer is formed so as to cover an other face side and a side face side of the glass substrate on which the first organic resin layer is formed. This further reinforces the glass substrate, whereby the edge part thereof can be more effectively prevented from chipping or cracking. Furthermore, the second organic resin layer is formed on the other face side and on the side face side of the glass substrate, which can further enhance the effect of preventing stray light and the effect of suppressing warping of the glass substrate.

Furthermore, preferably, a second organic resin layer is formed so as to cover the one face side and a side face side of the glass substrate on which the first organic resin layer is formed. This further reinforces the glass substrate, whereby the edge part thereof can be more effectively prevented from chipping or cracking. In addition, the second organic resin layer is formed on the one face side and on the side face side of the glass substrate, which can further enhance the effect of preventing stray light and which can ensure transparency for light incident to the other face side of the glass substrate, so as to maintain resolution.

In the foregoing scintillator panel, the second organic resin layer may be selected from silicone resin, urethane resin, epoxy resin, and fluorine resin.

Furthermore, a radiation detector according to the present invention comprises: the scintillator panel as described above; and a light receiving element arranged opposite to the scintillator layer on which the protection layer is formed.

In this radiation detector, the glass substrate with the thickness of not more than 150 μm serves as a support body of the scintillator panel, thereby to achieve excellent radiotransparency and flexibility and also relieve the problem of thermal expansion coefficient. In addition, in this radiation detector the first organic resin layer is formed so as to cover the entire surface of the glass substrate. This reinforces the glass substrate, whereby the edge part thereof can be prevented from chipping or cracking. Furthermore, stray light can be prevented from entering the side face of the glass substrate, and warping of the glass substrate can be suppressed because the first organic resin layer is formed on the entire surface thereof.

Advantageous Effect of Invention

The present invention has made it feasible to ensure satisfactory flexibility while preventing the glass substrate from chipping or cracking.

DESCRIPTION OF EMBODIMENTS

Preferred embodiments of the scintillator panel and the radiation detector according to the present invention will be described below in detail with reference to the drawings.

First Embodiment

Figure 1:
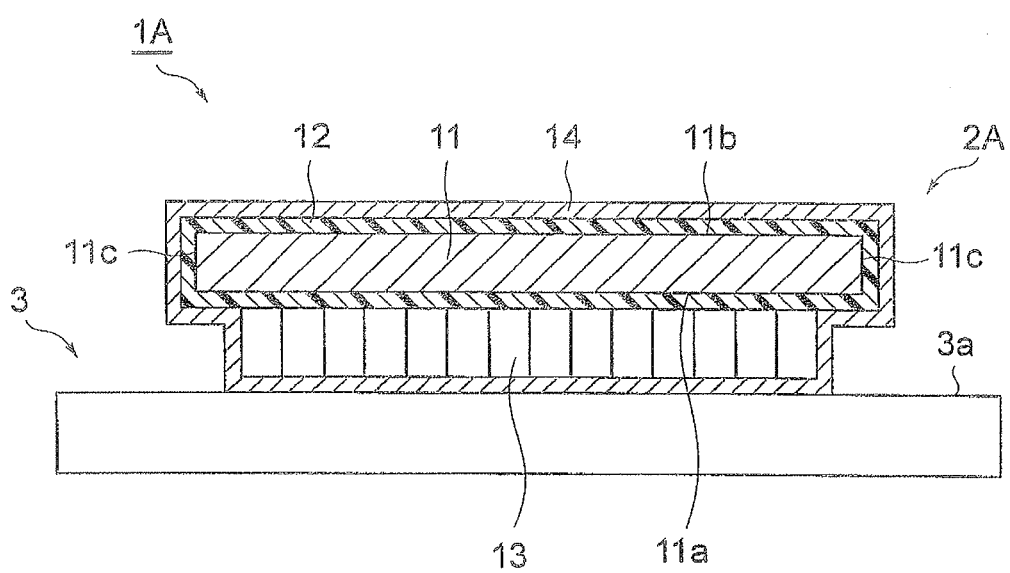
FIG. 1 is a cross-sectional view showing a configuration of a radiation detector according to the first embodiment of the present invention.

FIG. 1 is a cross-sectional view showing a configuration of a radiation detector according to the first embodiment of the present invention. As shown in the same drawing, the radiation detector 1A is constructed by fixing a light receiving element 3 to a scintillator panel 2A. The light receiving element 3 is, for example, a TFT panel in which photodiodes (PD) and thin-film transistors (TFT) are arrayed on a glass substrate.

The light receiving element 3 is stuck on a one face side of the scintillator panel 2A so that a light receiving surface 3a thereof is opposed to a below-described scintillator layer 13 in the scintillator panel 2A. The light receiving element 3 to be also used herein besides the TFT panel can be an element configured so that an image sensor such as CCD is connected through a fiber optic plate (FOP: an optical device composed of a bundle of several-micrometer optical fibers, e.g., J5734 available from Hamamatsu Photonics K.K.).

The scintillator panel 2A is composed of a glass substrate 11 as a support body, an organic resin layer (first organic resin layer) 12 to protect the glass substrate 11, a scintillator layer 13 to convert incident radiation to visible light, and a moisture-resistant protection layer 14 to protect the scintillator layer 13 from moisture.

The glass substrate 11 is, for example, an extremely thin substrate having the thickness of not more than 150 μm and preferably having the thickness of not more than 100 μm. Since the glass substrate 11 is extremely thin in thickness, it has sufficient radiotransparency and flexibility and ensures satisfactory shape-following capability of the scintillator panel 2A in sticking it on the light receiving surface 3a of the light receiving element 3.

The organic resin layer 12 is formed, for example, of poly-para-xylylene or polyurea or the like by vapor-phase deposition (e.g., evaporation), so as to cover the entire surface of the glass substrate 11. The thickness of the organic resin layer 12 is, for example, approximately from ten to several ten μm.

The scintillator layer 13 is formed on a one face 11a side of the glass substrate 11 on which the organic resin layer 12 is formed, for example, by growing and depositing columnar crystals of CsI doped with Tl by the evaporation method. The thickness of the scintillator layer 13 is, for example, 250 μm. The scintillator layer 13 is highly hygroscopic and could deliquesce with moisture in air if kept exposed to air. For this reason, the moisture-resistant protection layer 14 is needed for the scintillator layer 13.

The protection layer 14 is formed, for example, by growing poly-para-xylylene or the like by the vapor phase deposition such as the CVD method, so as to cover the scintillator layer 13 along with the glass substrate 11 on which the organic resin layer 12 is formed. The thickness of the protection layer 14 is, for example, approximately 10 μm.

In the radiation detector 1A having the configuration as described above, radiation incident from the glass substrate 11 side is converted to light in the scintillator layer 13 and the light is detected by the light receiving element 3. Since in the scintillator panel 2A the glass substrate 11 with the thickness of not more than 150 μm serves as a support body, it has excellent radiotransparency and flexibility.

The glass substrate 11 has sufficient flexibility, thereby satisfying the shape-following capability in sticking the scintillator panel 2A to the light receiving surface 3a of the light receiving element 3. Furthermore, when the TFT panel is used as the light receiving element 3 and when the light receiving surface 3a is a glass panel, the coefficient of thermal expansion of the light receiving surface 3a can be made equal to that of the glass substrate 11 of the scintillator panel 2A. This can prevent fine flaws on the glass substrate 11 or flaws made between the scintillator panel and the TFT panel by abnormally grown portions produced during formation of the scintillator layer 13 by evaporation, from transferring to the light receiving surface 3a because of heat during operation, and can also avoid the need for troublesome effort of calibration.

In addition, in this scintillator panel 2A the organic resin layer 12 is formed so as to cover the entire surface of the glass substrate 11. This reinforces the glass substrate 11, whereby the edge part thereof can be prevented from chipping or cracking. This also contributes to improvement in handling performance during manufacture and during use. Furthermore, stray light can be prevented from entering a side face 11c of the glass substrate 11 and, since the organic resin layer 12 is formed on the entire surface, it becomes possible to suppress warping of the glass substrate 11 due to internal stress after formation of the scintillator layer 13. The effect of suppressing warping of the glass substrate 11 becomes particularly prominent in a case where the glass substrate 11 is a small substrate of about 10 cm×10 cm.

Moreover, since the organic resin layer 12 is formed so as to cover the entire surface of the glass substrate 11, it also becomes possible to adjust the surface condition of the glass substrate 11 so as to achieve appropriate surface energy and surface roughness in formation of the scintillator layer 13.

Second Embodiment

Figure 2:
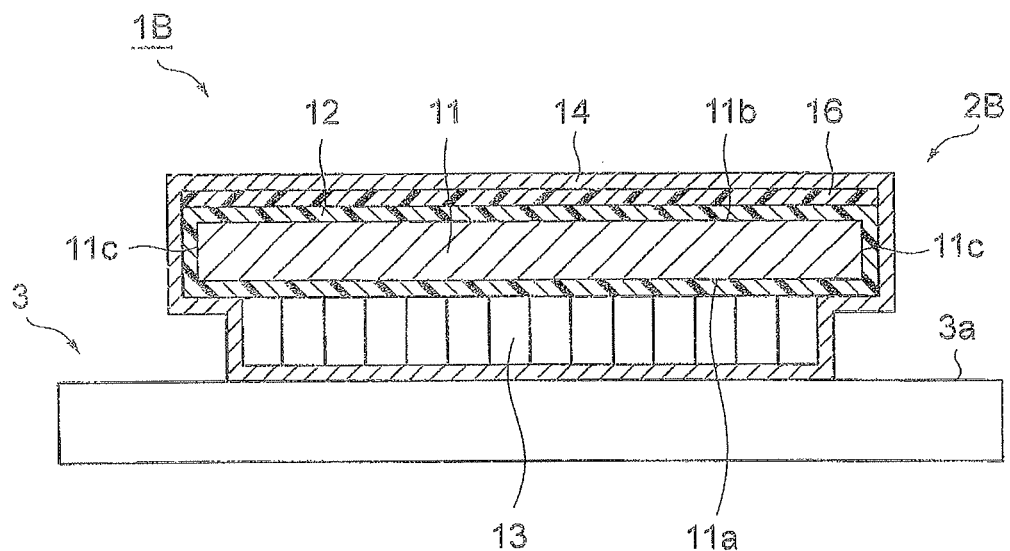
FIG. 2 is cross-sectional views showing configurations of radiation detectors according to the second embodiment of the present invention.
Figure 2:
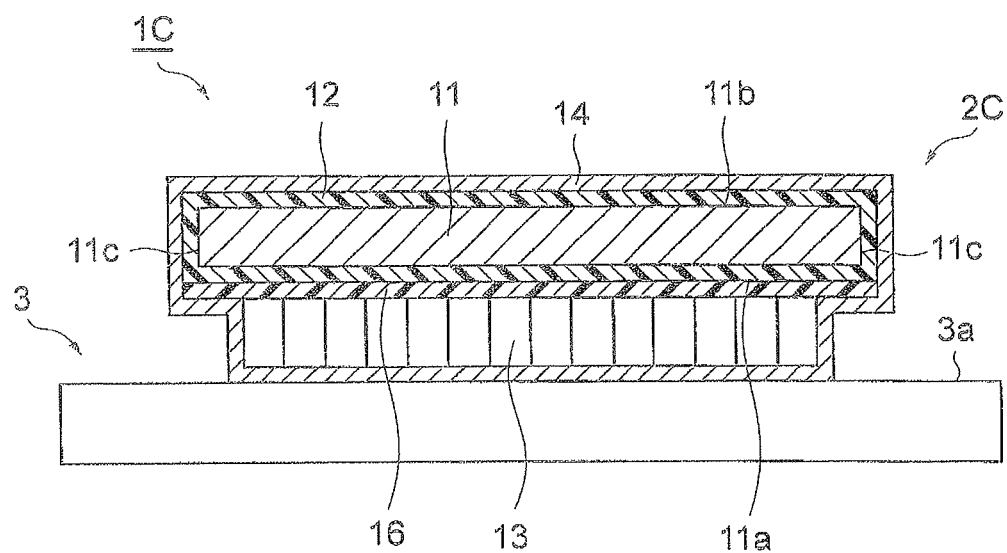

FIG. 2 is cross-sectional views showing configurations of radiation detectors according to the second embodiment of the present invention. As shown in the same drawing, the radiation detectors 1B, 1C according to the second embodiment are different from the first embodiment in that in scintillator panels 2B, 2C, a resin film layer 16 is further arranged outside the glass substrate 11 on which the organic resin layer 12 is formed.

More specifically, in the example shown in FIG. 2(a), the resin film layer 16 is stuck on the opposite face (other face 11b) side to the face where the scintillator layer 13 is formed, in the glass substrate 11 on which the organic resin layer 12 is formed, by means of a laminator or the like. Furthermore, in the example shown in FIG. 2(b), the resin film layer 16 is stuck on the face (one face 11a) side where the scintillator layer 13 is formed, in the glass substrate 11 on which the organic resin layer 12 is formed, by means of a laminator or the like.

The resin film layer 16 is selected, for example, from PET (polyethylene terephthalate), PEN (polyethylene naphthalate), COP (cycloolefin polymer), and PI (polyimide). The thickness of the resin film layer 16 is, for example, approximately from ten to several ten μm as the organic resin layer 12 is. Furthermore, the edge of the resin film layer 16 is preferably coincident with the edge of the glass substrate 11 or slightly projects out therefrom.

In this configuration, just as in the above embodiment, the glass substrate 11 is also reinforced by the organic resin layer 12, whereby the edge part thereof can be prevented from chipping or cracking. In addition, stray light can be prevented from entering the side face 11c of the glass substrate 11 and, since the organic resin layer 12 is formed on the entire surface, warping of the glass substrate 11 can be suppressed.

Furthermore, in these radiation detectors 1B, 1C, the glass substrate 11 is further reinforced by addition of the resin film layer 16, whereby the edge part thereof can be more securely prevented from chipping or cracking. When the resin film layer 16 is arranged on the other face 11b side of the glass substrate 11 as shown in FIG. 2(a), internal stress of the scintillator layer 13 can be cancelled, so as to more effectively suppress warping of the glass substrate 11. When the resin film layer 16 is arranged on the one face 11a side of the glass substrate 11 as shown in FIG. 2(b), transparency can be ensured for light incident to the other face 11b side of the glass substrate 11, so as to decrease reflection toward the light receiving element 3, with the result that resolution can be maintained.

Third Embodiment

Figure 3:
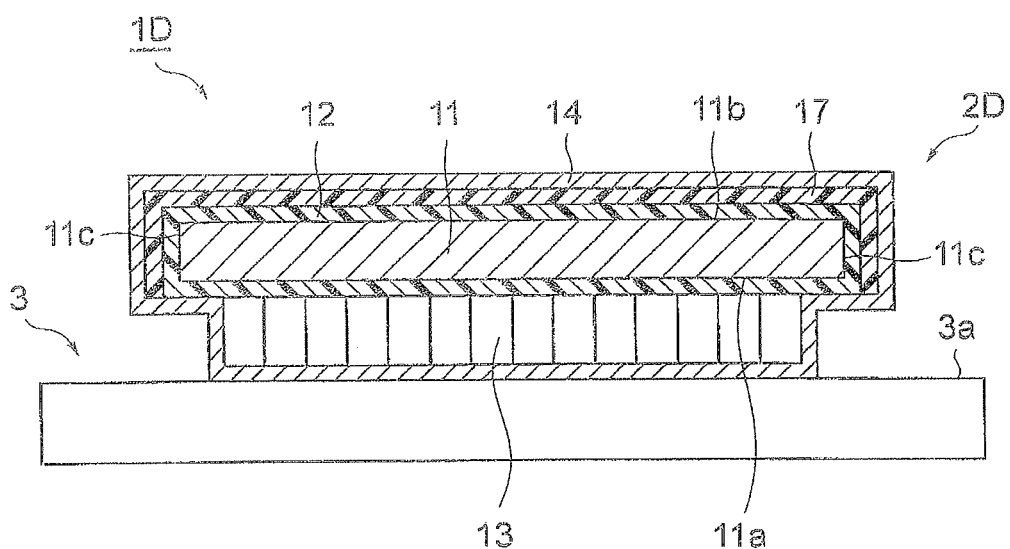
FIG. 3 is cross-sectional views showing configurations of radiation detectors according to the third embodiment of the present invention.
Figure 3:
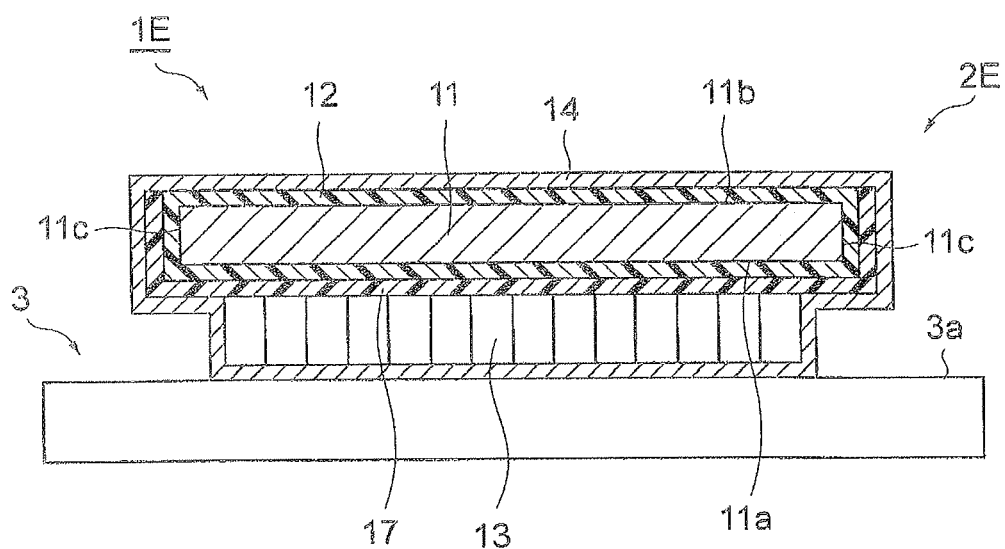

FIG. 3 is cross-sectional views showing configurations of radiation detectors according to the third embodiment of the present invention. As shown in the same drawing, the radiation detectors 1D, 1E according to the third embodiment are different from the first embodiment in that in scintillator panels 2D, 2E, an organic resin layer (second organic resin layer) 17 is further arranged outside the glass substrate 11 on which the organic resin layer 12 is formed.

More specifically, in the example shown in FIG. 3(a), the organic resin layer 17 is formed so as to cover the opposite face (other face 11b) to the face where the scintillator layer 13 is formed, and the side face 11c, in the glass substrate 11 on which the organic resin layer 12 is formed. Furthermore, in the example shown in FIG. 3(b), the organic resin layer 17 is formed so as to cover the face (one face 11a) where the scintillator layer 13 is formed, and the side face 11c, in the glass substrate 11 on which the organic resin layer 12 is formed.

The organic resin layer 17 to be used herein can be, for example, silicone resin, urethane resin, epoxy resin, fluorine resin, or the like. A method for forming the organic resin layer 17 is, for example, coating by the spin coating method or the like. The thickness of the organic resin layer 17 is, for example, approximately from ten to several ten μm as the organic resin layer 12 is.

In these configurations, just as in the above embodiments, the glass substrate 11 is also reinforced by the organic resin layer 12, whereby the edge part thereof can be prevented from chipping or cracking. In addition, stray light can be prevented from entering the side face 11c of the glass substrate 11 and, since the organic resin layer 12 is formed on the entire surface, warping of the glass substrate 11 can be suppressed.

Furthermore, in these radiation detectors 1D, 1E, the glass substrate 11 is further reinforced by addition of the organic resin layer 17, whereby the edge part thereof can be more securely prevented from chipping or cracking. When the organic resin layer 17 is formed so as to cover the other face 11b and the side face 11c of the glass substrate 11 as shown in FIG. 3(a), it is feasible to further enhance the effect of preventing stray light from entering the side face 11c and the effect of suppressing warping of the glass substrate 11. When the organic resin layer 17 is formed so as to cover the one face 11a and the side face 11c of the glass substrate 11 as shown in FIG. 3(b), the effect of preventing stray light from entering the side face 11c can be enhanced, and transparency can be ensured for light incident to the other face 11b side of the glass substrate 11, so as to decrease reflection toward the light receiving element 3, with the result that resolution can be maintained.

REFERENCE SIGNS LIST 1A-1E radiation detectors; 2A-2E scintillator panels; 3 light receiving element; 11 glass substrate; 11a one face; 11b other face; 11c side face; 12 organic resin layer (first organic resin layer); 13 scintillator layer; 14 protection layer; 16 resin film layer; 17 organic resin layer (second organic resin layer).

The invention claimed is:

1. A scintillator panel comprising:
   a glass substrate with a thickness of not more than 150 μm having radiotransparency;
   a first organic resin layer formed so as to cover the entire surface of the glass substrate;
   a scintillator layer formed on a one face side of the glass substrate on which the first organic resin layer is formed;
   a moisture-resistant protection layer formed so as to cover the scintillator layer along with the glass substrate on which the first organic resin layer is formed,
   wherein a resin film layer is stuck between an other face side of the glass substrate on which the first organic resin layer is formed, and the protection layer.

2. The scintillator panel according to claim 1, wherein the first organic resin layer is selected from poly-para-xylylen and polyurea.

3. The scintillator panel according to claim 1, wherein the resin film layer is selected from PET, PEN, COP, and PI.

4. A radiation detector comprising:
   the scintillator panel as set forth in claim 1; and
   a light receiving element arranged opposite to the scintillator layer on which the protection layer is formed.

* * * * *